(12) United States Patent
Ezekiel

(10) Patent No.: US 7,803,619 B2
(45) Date of Patent: Sep. 28, 2010

(54) EMBRYOID BODY-BASED SCREEN

(75) Inventor: Uthayashanker Ezekiel, St. Louis, MO (US)

(73) Assignee: Geneprotech, Inc., St. Louis, MO (US)

( * ) Notice: Subject to any disclaimer, the term of this patent is extended or adjusted under 35 U.S.C. 154(b) by 643 days.

(21) Appl. No.: 11/456,203

(22) Filed: Jul. 9, 2006

(65) Prior Publication Data

US 2007/0015210 A1 Jan. 18, 2007

Related U.S. Application Data

(63) Continuation-in-part of application No. 10/997,203, filed on Nov. 24, 2004, now abandoned.

(51) Int. Cl.
  *C12N 5/00* (2006.01)
  *C12N 5/02* (2006.01)
  *C12N 5/07* (2006.01)
  *C12N 5/10* (2006.01)

(52) U.S. Cl. .................. 435/377; 435/375; 435/383; 435/325; 435/354

(58) Field of Classification Search ................. 435/325
See application file for complete search history.

(56) References Cited

U.S. PATENT DOCUMENTS 7,547,547 B2 * 6/2009 Dang et al. ................. 435/382
2004/0096432 A1 * 5/2004 Fleischmann et al. .... 424/93.21

OTHER PUBLICATIONS

Ng, Hematopoiesis, 2005, 106:1601-1603.*
Ruhnke, 2003, Stem Cells, 21:428-436.*
Keller, G., 2005, Genes and Development, 19:1129-1155.*
Wang et al, 2005, BBRC, 330:934-942.*
Ng et al, 2005, Blood, 106:1601-1603.*
Uetsuki et al, 1996, Journal of Biological Chemistry, 271:918-924.*
Ezekial U et al, 2007, Electronic Journal of Biotechnology, 10:328-335.*
Conley BJ et al, 2004, Int Jour Biochem Cell Biol., 36:555-567.*
Valamehr, 2008, PNAS, 105:14459-14464.*
Mohr, Biomaterials, 2006, 27:6032-6042.*
Torisawa et al, 2007, Lab Chip, 7:770-776.*
Carpenedo, Stem Cells, 2007, 25:2224-2234.*
Dang et al., Biotechnol. Bioeng., 78:442-453 (2002).
Smith, A.G., Annu. Rev. Cell. Dev. Biol., 17:435-462 (2001).
Chen et al., Genes Dev., 8:2466-2477 (1994).
Larue et al., Development, 122:3185-3194 (1996).
Sauer et al., Am. J. Pathol., 156:151-158 (2000).

* cited by examiner

*Primary Examiner*—Valarie Bertoglio
(74) *Attorney, Agent, or Firm*—Joseph E. Zahner

(57) ABSTRACT

Disclosed are embryoid bodies having a uniform size of approximately 415 nm and comprising genetically modified embryonic stem cells, and methods of making same. The genetically uniform embryoid bodies can be multiplexed as one embryoid body per well in a multiwell format, and used as a high to medium throughput screen for test agents that affect the development and homeostasis of animals, including humans. The genetic modification of the embryonic stem cells is a promoter-report-selection construct that enables the selection and detection of cells of a particular lineage in the EB, to determine the effects of a test agent.

7 Claims, 5 Drawing Sheets

EMBRYOID BODY-BASED SCREEN

This application is a continuation-in-part of U.S. patent application Ser. No. 10/997,203, which was filed on Nov. 24, 2004 now abandoned. U.S. patent application Ser. No. 10/997,203 is incorporated herein in its entirety by reference.

BACKGROUND OF THE INVENTION

1. Field of the Invention

The invention relates to embryoid body systems and methods employing embryoid bodies for the screening of chemical and biological agents for safety and effectiveness.

2. Description of the Related Art

Embryonic stem (ES) cells are pluripotent cells derived from an early embryonic stage of development. When cultured in the presence of leukocyte inhibitory factor (LIF), ES cells remain undifferentiated. Removal of LIF and regulation of culture conditions lead to ES cell differentiation into specific cell types [1-7]. Many differentiation strategies involve the generation of embryoid bodies (EB) that are aggregates of ES cells in suspension [8]. The addition of small molecules to EB has three potential outcomes: 1) increased differentiation of EB into particular lineages or cell types; 2) toxic effects on the EB; or 3) inhibition of particular lineages or cell types. As an example, the presence of the small molecule retinoic acid (RA) at an appropriate time point is one strategy for differentiation of ES cells into neuronal cell types. An object of this invention is that embryoid bodies (which contain all germ layers: ectoderm, mesoderm, endoderm) are useful for the study of small molecule effects on differentiation of ES cells into cell types of each germ layer.

ES cells are totipotent and have been used as model systems for differentiation studies. ES cells are derived from the inner cell mass of developing blastocysts, are maintained in culture under appropriate conditions (such as growth on embryonic fibroblasts in the presence of LIF) where they retain their totipotency and are able to generate all cell lineages after introduction into host blastocysts [9-11]. Using appropriate culture conditions, ES cells differentiate and form EBs that contain cells of hematopoietic, endothelial, muscular and neuronal lineages [6, 7, 12, 13]. Many aspects of lineage-specific differentiation programs observed within EBs reflect those found in the embryo, indicating that this model system provides access to early cell populations that develop in a normal fashion. ES cells are also able to spontaneously differentiate and generate various lineages under appropriate conditions in cell culture [6, 7, 12, 13]. The in vitro differentiation potential of ES cells allows their use as a model system for the study of developmental potential and also as a valuable reagent for stem cell therapeutic approaches. The instant invention disclosed herein is directed to an efficient in vitro system to screen and study effects of small molecules and bioagents, and is an alternative to embryo and live animal studies. Using this in vitro system, it is possible to screen many compounds efficiently and, once a candidate molecule is identified, this agent can be studied thoroughly to define how it exerts its effect.

Embryoid Bodies

ES cells are pluripotent and derived from the inner cell mass of the early embryo. When murine ES cells are cultured in the presence of embryonic fibroblasts and LIF, they remain undifferentiated and maintain the capacity to differentiate into any cell type. When cultured in the absence of LIF and grown in suspension, murine ES cells form three-dimensional aggregates of cells called embryoid bodies (EB) (FIG. 1A). Over time, the EB gives rise to all three embryonic germ layers [14, 15]. EB are usually generated by a hanging drop method in which the cells are allowed to aggregate in a hanging drop or a stirred culture method [8]. In the stirred culture method, a large quantity of EB are formed but become fused because of cell collisions [8]. In the hanging drop method, the EB size is uniform since each drop contains a limited and known number of ES cells. It has been postulated that EB formation occurs by a calcium-dependent cell-cell adhesion-mediated mechanism. A role for E-cadherin has been identified since E-cadherin$^{-/-}$ ES cells are defective in aggregate formation [16]. The surface expression of E-cadherin decreases as ES cells initiate differentiation as exemplified by the report that E-cadherin surface expression is approximately 100% on day 0-3, and drops to 15% on day 6 [16] of differentiation. Of particular relevance to this invention, it has been identified that the differentiation pattern of EB recapitulates early embryogenesis in many ways [14-17]. Therefore, studying the effect of small molecules on EB will shed light on small molecule mechanisms of action better than will a similar study in a single type of cells. For example, the drug thalidomide showed no anti-angiogenic effect when screened in an endothelial cell culture system or chorioallantoic membrane assay; however, since use of EB recapitulates intact embryo development, it was demonstrated that thalidomide had anti-angiogenic effect [17]. The use of EB is therefore a powerful way to study and screen compounds for physiologically relevant results.

Promoter

Table 1 depicts various promoters, which serve as useful examples in the practice of this invention.

| GENE/Promoters | ORGANISM | REGION |
|---|---|---|
| NERVOUS SYSTEM | | |
| HES-5 | MOUSE | n. precursor sp-mouse helix-loop-helix |
| ChAT | MOUSE | cholinergic |
| aromatic L-amino acid decarboxylase | HumAN | substantia nigra (SN), the ventral tegmental area (VTA) and the dorsal, medial and pontine raphe nuclei |
| GRIK5 (glutamate receptor ionotropic kainate-5) | | |
| Myelin Basic Protein-MBP | human | oligodendrocyte |
| GABA(A) receptor delta subunit | | |
| calmodulin II | rat | neuron-specific |

-continued

| GENE/Promoters | ORGANISM | REGION |
|---|---|---|
| calcium/calmodulin-dependent kinase II (CaMKII)- alpha | | forbrain/hippocampus |
| calmodulin III | rat | prominently in pyramidal cells of the cerebral neocortex and the hippocampal regions CA1 to CA3, in Purkinje cells of the cerebellar cortex, and in neurons of the spinal cord, and moderately in granule cells of the dentate gyrus and the cerebellar cortex |
| T alpha 1 alpha-tubulin promoter | | specific to the CNS and PNS, with expression in vivo at embryonic day 13.5 |
| dopamine beta-hydroxylase | | |
| GAP 43 | RAT | expression in a neuronal-specific manner |
| glutamate decarboxylase 65 gene (gad65) | MOUSE | GABAergic neurons |
| amyloid precursor protein promoter | HUMAN | hippocampal pyramidal neurons, neurons in the deeper layers of cerebral cortex, and in thalamic nuclei |
| Choline acetyltransferase (ChAT) | mouse | cholinergic neurons |
| neuronal nicotinic acetylcholine receptor alpha4 gene-nAChR | | |
| myelin basic protein (MBP) | mouse | oligodendrocyte specific |
| GABA(A) receptor delta subunit | mouse | cerebral cortex, hippocampal formation, thalamus, and brainstem -consistent with endogenous pattern, except cerebellum -expressed in purkinje not in cortcal neurons |
| GAP-43 | mouse | hippocampal mossy cells |
| Necdin-postmitotic neuron-restrictive core promoter | mouse | Post-mititic neurons |
| neuron-specific enolase (NSE) promoter | mouse | embryonic stem (ES) cells and preimplantation embryos |
| dopamine beta-hydroxylase gene promoter | | classic noradrenergic brain stem nuclei, sympathetic ganglion neurons, and adrenal chromaffin cells |
| Purkinje cell-specific L7 protein | mouse | cerebellar Purkinje cells and retinal bipolar neurons |
| NDRF (neuroD-related factor) | mouse | neural development |
| Glial fibrillary acidic protein (GFAP) | | ASTROCYTE |
| | | SKIN |
| Keratin 15 (Krt 15) | mouse | Putative Epithelial Stem Cells in hair follicle |
| keratin 12 (Krt12) | | corneal epithelium |
| | | LUNG SPECIFIC |
| surfactant protein C (SP-C) promoter | human | alveolar epithelial type II cell-specific promoter |
| CC10 gene | | epithelial cells lining the trachea, bronchi, and bronchioles |
| | | LIVER |
| Albumin | mouse | liver specific |
| hepatocyte-specific promoter element HP1 | mouse | liver specific |
| apoE | human | liver specific |
| platelet factor 4 promoter (PF4) | mouse | megakaryocytes and platelets |
| Vav prmoter | mouse | hematopoietic tissues |
| hCD2 promoter and locus control region (LCR). | human | T and B lymphocytes |
| CD19 | | B lymphocyte |
| | | reproductive tissues |
| Pgk-2 promoter | mouse | spermatocyte |
| protamine (prm1) | mouse | male germ line-spermatids |
| zona pellucida (Zp3) | | maturing oocyte (oogenesis) |
| PDX-1 | | early embryogenesis-entire pancreatic epithelium, including both endocrine (hormone-producing) and exocrine (enzyme-producing) cells, as well as subpopulationsof duodenal and gastric enteroendocrine cells. Adult stage- abundant in beta cells with lower levels in acinar cells |
| transthyretin promoter | | fetal and adult liver |
| fatty acid-binding protein gene | | (gut stem cells) transitional epithelium that lines the renal calyces and pelvis, ureters, and bladder |
| alpha-myosin heavy chain promoter | | cardiomyocytes |
| smooth muscle myosin heavy chain (smMHC) | | all smooth muscles |

The neuron-specific promoter necdin is used for the study examples disclosed in this application. Differentiation of mammalian neurons during development is a very complex process involving regulation and coordination of gene expression at multiple stages [18, 19, 20]. The P19 embryonic carcinoma cell line is frequently used as a model system for neuronal differentiation. Exposure of aggregated P19 cells to retinoic acid (RA) results in differentiated cells that have many fundamental characteristics similar to neurons. From RA-differentiated and undifferentiated P19 cells, a subtractive cDNA library was made and from that library, the necdin gene was identified [21]. The necdin gene encodes a protein of 325 amino acids and contains no intronic regions [22]. The 5' flanking region of the transcription start site contains promoter activity. The use of the necdin promoter as an example for this application is of importance because the necdin gene is expressed in all terminally differentiated post-mitotic neurons but not in undifferentiated stem cells [21, 23, 24,]. In humans, the necdin gene has been mapped to chromosome 15q that contains the autistic susceptibility region. Chromosome 15q is implicated in neurodevelopmental disorders including Prader-Willi syndrome, Angelman syndrome, autism and developmental abnormalities resulting from chromosomal deletions or duplications in this region [25]. Exclusive expression of necdin in post-mitotic neurons may contribute to permanent neuronal mitotic arrest. Therefore, placement of selection and reporter genes under the control of the necdin promoter as proposed in this study will allow for exclusive expression of these genes in post-mitotic neurons.

Selection Markers Puromycin ($Pur^r$) and Hygromycin-B Phosphotransferase ($Hyg^r$)

Puromycin is an aminonucleoside antibiotic produced by *Streptomyces alboniger*. Puromycin specifically inhibits peptidyl transfer on the ribosome and therefore inhibits growth of eukaryotic cells. Expression of the puromycin-N-acetyltransferase (pac) gene from *S. alboniger* confers puromycin resistance ($Pur^r$) in transfected cells. Hygromycin-B is an aminocyclitol that inhibits protein synthesis by disrupting translocation and promoting mistranslation. The hygromycin-B phosphotransferase gene product detoxifies hygromycin-B by phosphorylation. The $Hyg^r$ and $Pur^r$ resistance markers have been chosen for this study because of their use as selection markers in several cell model systems including ES cells and neuronal cell lines [26].

Internal Ribosome Entry Site (IRES) and β-Galactosidase Reporter Gene

The presence of an internal ribosomal entry site (IRES) allows for dual and simultaneous expression of two genes. The IRES isolated from the encephalomyocarditis virus permits the translation of two open reading frames from one messenger RNA [29]. The lacZ reporter gene from *E. coli* encodes the enzyme β-galactosidase [27, 28]. When β-galactosidase cleaves substrate, 5-bromo-4-chloro-3-indolyl-β-D-galactopyranoside (X-gal), a blue insoluble precipitate forms in the cells that is detectable by light microscopy. Using an X-gal staining method, the presence of β-galactosidase-positive cells will be qualitatively identified by the presence of blue precipitate and quantitatively detected using a highly sensitive chemiluminescence method [29]. Of importance to this quantitative detection method is the fact that the reaction pH is optimal only for bacterial β-galactosidase but not endogenous eukaryotic enzyme activity [29].

Differentiation of ES Cells into a Neuronal Lineage

ES cells are derived from the inner cell mass of developing blastocysts [11, 30]. When grown on embryonic fibroblasts in the presence of LIF, ES cells maintain their totipotential capacity and are able to generate cells of all lineages including germ layers after being introduced into host blastocysts [11, 30]. Using homologous recombination to introduce mutations into ES cells, it has been observed that the mutations are carried into the germ line and therefore lead to the generation of knockout mice with specific mutations [11]. Using appropriate conditions, ES cells generate various cell lineages in vitro. For example, ES cells maintained in suspension (that is, not allowed to attach) and in the absence of LIF form spheroid colonies of differentiated cells known as EB (FIG. 1A of Preliminary Studies). EB contain many different types of precursor and other cell types, for example, cells of the hematopoietic, endothelial, muscular and neuronal lineages. By maintaining EB under specific culture conditions and addition of factors specific for differentiation of particular cell lineages, specific cell types can be generated [3, 5, 13, 20, 31]. There are several well-established protocols for efficiently deriving neural cells from ES cells [4, 20, 32, 33]. All of these protocols begin with EB formation. Methods utilizing RA for neuronal differentiation result in the formation of neuronal progenitor cells during early differentiation and the formation of neurons, glial cells and astrocytic cells during the later stages [3-5, 13, 20, 21, 33]. Protocols using growth factors such as fibroblast growth factor (FGF)-2 generate large numbers of neural precursor cells and cause synchronized differentiation of neurons [20, 33-35]. Neuronal cell types are identified by the presence of specific antigenic markers detectable by immunostaining (e.g., neuronal precursor cells are identified by the presence of nestin; astrocytes are identified by glial fibrillary acidic protein [GFAP]; oligodendrocytes are identified by the presence of a sulfatide differentiation marker specifically on the surface of oligodendrocytes called O4 antigen [36], and post-mitotic neurons are identified by the presence of microtubule associated protein (MAP)2, MAP5, neural filament (NF) 200 and synaptophysin [32, 37, 38]. ES cells treated with RA differentiate into neuronal-glial precursor cells and then into glial cells and functional neurons in vitro. Fraichard et al [32] have shown the kinetics of differentiation of various populations of neuronal cell types arising from RA treatment of ES cells and the results indicate that neuronal-glial precursor cells predominate at day 3, oligodendrocytes at day 5, astrocytes at days 6 to 9 and neuronal cells at days 5 to 20. Specific results indicate that 25% of the cells on day 9 are neuronal and the remaining 75% are astrocytes [32]. Of interest, astrocytic cells decrease in abundance after day 9 and neuron-positive cells increase in abundance [32]. Since RA causes ES cells to differentiate into neuronal cell types, RA is used as one of the small molecule compounds in the present study as a positive control.

Generation of Stable ES Cell Lines

In experiments designed in this proposal, a neuron-specific promoter with a selection cassette is introduced into ES cells at a single locus. Use of site-specific integration is desirable since many problems related to random integration, such as inactivation of genes, are avoidable. The hypoxanthine phosphoribosyl transferase (HPRT) gene is expressed during all stages of development of ES cells thereby suggesting that the locus remains in open chromatin configuration constitutively [39]. This finding offers the suggestion that HPRT-specific promoters and enhancers retain their natural specificity in differentiated tissues and cell types [39]. This approach is preferred when a strong promoter is used in the study. When working with weak promoters, stable ES cell lines will be generated by random integration since this methodology (advantageously in this case) leads to more than one copy integration. The protein encoded by the HPRT gene is involved in the salvage pathway of nucleotide metabolism and the HPRT gene has nine exons spread over a 33 Kb region of the X chromosome [40]. Cells with a mutated HPRT gene will survive when grown in the presence of the nucleotide analogue, 6-thioguanine (6-TG), but cells with wild type HPRT will not. The presence of 6-TG in the culture media causes incorporation of 6-TG into the nucleotide pool which, when incorporated by the HPRT enzyme, leads to cell death. When the HPRT gene is disrupted, the cells survive in 6-TG because the nucleotide analogue is not incorporated into the DNA. Therefore, 6-TG selection offers a powerful way to screen cells for a targeted HPRT locus.

Small Molecules and Growth Factors

It has been reported that small molecules exert effects during differentiation [41, 42]. RA is an active metabolite of Vitamin A, differentiates ES cells to neuronal lineages [32] and acts through kinase-dependent pathways in neurogenesis [43]. Resveratrol, a natural compound present in grape skins, acts on the extracellular signal-regulated kinase (ERK)-1 pathway in undifferentiated and differentiated neuron-like cells [44]. Neuroprotective effects of Ginkgo biloba extracts have been demonstrated in vitro and in vivo [45, 46]. Natural compounds such as lignans play a role in neuronal differentiation [47] and boswellic acid acetate from the herb Boswellia carterii induces differentiation of myeloid leukemia HL60 cells into monocyte-like cells [48]. An analog of Vitamin D having two double bonds in the side chain causes differentiation of MG-63 human osteosarcoma cells into osteoblasts [49]. Takahashi et al screened 880 compounds approved for human use and tested these compounds for their ability to induce cardiac differentiation of murine ES cells [50] by tagging the ES cells with a cardiac myosin heavy chain promoter driving enhanced green fluorescent protein (EGFP) expression. They found that treatment of murine ES cells with vitamin C (aka ascorbic acid) markedly increased the number of cardiac myocytes spontaneously showing rhythmic contractile activity and staining positive for sarcomeric myosin and alpha-actinin [50].

LITERATURE CITED

The following references are cited throughout this disclosure to illuminate the instant invention. These references are incorporated herein by reference. Applicant reserves the right to challenge the veracity of any statement made in any of these references.

[1] H. Q. Xian and D. I. Gottlieb, *Peering into early neurogenesis with embryonic stem cells*. Trends Neurosci 24, 685-686 (2001).

[2] G. Bain and D. I. Gottlieb, Neural cells derived by in vitro differentiation of P19 and embryonic stem cells. Perspect Dev Neurobiol 5, 175-178 (1998).

[3] R. M. Schmitt, E. Bruyns and H. R. Snodgrass, Hematopoietic development of embryonic stem cells in vitro: cytokine and receptor gene expression. Genes Dev 5, 728-740 (1991).

[4] G. Bain, D. Kitchens, M. Yao, J. E. Huettner and D. I. Gottlieb, *Embryonic stem cells express neuronal properties in vitro*. Dev Biol 168, 342-357 (1995).

[5] A. Y. Chiu and M. Rao, Human Embryonic Stem Cells, Humana Press, New Jersey, 2003.

[6] M. W. McBurney, E. M. Jones-Villeneuve, M. K. Edwards and P. J. Anderson, *Control of muscle and neuronal differentiation in a cultured embryonal carcinoma cell line*. Nature 299, 165-167 (1982).

[7] G. Keller, M. Kennedy, T. Papayannopoulou and M. V. Wiles, *Hematopoietic commitment during embryonic stem cell differentiation in culture*. Mol Cell Biol 13, 473-486 (1993).

[8] S. M. Dang, M. Kyba, R. Perlingeiro, G. Q. Daley and P. W. Zandstra, Efficiency of embryoid body formation and hematopoietic development from embryonic stem cells in different culture systems. Biotechnol Bioeng 78, 442-453 (2002).

[9] A. Nagy, E. Gocza, E. M. Diaz, V. R. Prideaux, E. Ivanyi, M. Markkula and J. Rossant, *Embryonic stem cells alone are able to support fetal development in the mouse*. Development 110, 815-821 (1990).

[10] A. Bradley, M. Evans, M. H. Kaufman and E. Robertson, *Formation of germ-line chimaeras from embryo-derived teratocarcinoma cell lines*. Nature 309, 255-256 (1984).

[11] I. J. Jackson and C. M. Abbott, Mouse Genetics and Transgenics-A Practical Approach, Oxford University Press Inc. New York, 2000.

[12] J. S. Odorico, D. S. Kaufman and J. A. Thomson, *Multilineage differentiation from human embryonic stem cell lines*. Stem Cells 19, 193-204 (2001).

[13] F. A. Brook and R. L. Gardner, *The origin and efficient derivation of embryonic stem cells in the mouse*. Proc Natl Acad Sci USA 94, 5709-5712 (1997).

[14] A. G. Smith, *Embryo-derived stem cells: of mice and men*. Annu Rev Cell Dev Biol 17, 435-462 (2001).

[15] W. S. Chen, K. Manova, D. C. Weinstein, S. A. Duncan, A. S. Plump, V. R. Prezioso, R. F. Bachvarova and J. E. Darnell, Jr., *Disruption of the HNF-4 gene, expressed in visceral endoderm, leads to cell death in embryonic ectoderm and impaired gastrulation of mouse embryos*. Genes Dev 8, 2466-2477 (1994).

[16] L. Larue, C. Antos, S. Butz, O. Huber, V. Delmas, M. Dominis and R. Kemler, *A role for cadherins in tissue formation*. Development 122, 3185-3194 (1996).

[17] H. Sauer, J. Gunther, J. Hescheler and M. Wartenberg, Thalidomide inhibits angiogenesis in embryoid bodies by the generation of hydroxyl radicals. Am J Pathol 156, 151-158 (2000).

[18] G. Bain, W. J. Ray, M. Yao and D. I. Gottlieb, Retinoic acid promotes neural and represses mesodermal gene expression in mouse embryonic stem cells in culture. Biochem Biophys Res Commun 223, 691-694 (1996).

[19] O. Brustle, A. C. Spiro, K. Karram, K. Choudhary, S. Okabe and R. D. McKay, *In vitro-generated neural precursors participate in mammalian brain development*. Proc Natl Acad Sci USA 94, 14809-14814 (1997).

[20] M. Li, L. Pevny, R. Lovell-Badge and A. Smith, Generation of purified neural precursors from embryonic stem cells by lineage selection. Curr Biol 8, 971-974 (1998).

[21] K. Maruyama, M. Usami, T. Aizawa and K. Yoshikawa, A novel brain-specific mRNA encoding nuclear protein (necdin) expressed in neurally differentiated embryonal carcinoma cells. Biochem Biophys Res Commun 178, 291-296 (1991).

[22] E. Maruyama, Biochemical characterization of mouse brain necdin. Biochem J 314 (Pt 3), 895-901 (1996).

[23] R. Takazaki, I. Nishimura and K. Yoshikawa, Necdin is required for terminal differentiation and survival of primary dorsal root ganglion neurons. Exp Cell Res 277, 220-232 (2002).

[24] H. Taniura, N. Taniguchi, M. Hara and K. Yoshikawa, Necdin, a postmitotic neuron-specific growth suppressor, interacts with viral transforming proteins and cellular transcription factor E2F1. J Biol Chem 273, 720-728 (1998).

[25] T. K. Chibuk, J. M. Bischof and R. Wevrick, A necdin/MAGE-like gene in the chromosome 15 autism susceptibility region: expression, imprinting, and mapping of the human and mouse orthologues. BMC Genet 2, 22 (2001).

[26] K. L. Tucker, Y. Wang, J. Dausman and R. Jaenisch, *A transgenic mouse strain expressing four drug-selectable marker genes*. Nucleic Acids Res 25, 3745-3746 (1997).

[27] K. Hidaka, G. An, P. Ip, M. Kuwana and L. Siminovitch, *Amphotericin B enhances efficiency of DNA-mediated gene transfer in mammalian cells*. Somat Cell Mol Genet 11, 109-115 (1985).

[28] J. Celis, Cell Biology. A Laboratory Handbook, Academic Press, Boston, Mass., 2002.

[29] I. Bronstein, B. Edwards and J. C. Voyta, 1,2-*dioxetanes: novel chemiluminescent enzyme substrates. Applications to immunoassays*. J Biolumin Chemilumin 4, 99-111 (1989).

[30] E. Robertson, Embryo-derived stem cell lines. In Teratocarcinoma and Embryonic Stem Cells.-a Practical Approach, IRL Press, Washington, D.C., 2002.

[31] K. S. O'Shea, *Embryonic stem cell models of development*. Anat Rec 257, 32-41 (1999).

[32] A. Fraichard, O. Chassande, G. Bilbaut, C. Dehay, P. Savatier and J. Samarut, *In vitro differentiation of embryonic stem cells into glial cells and functional neurons*. J Cell Sci 108 (Pt 10), 3181-3188 (1995).

[33] C. R. Hancock, J. P. Wetherington, N. A. Lambert and B. G. Condie, *Neuronal differentiation of cryopreserved neural progenitor cells derived from mouse embryonic stem cells*. Biochem Biophys Res Commun 271, 418-421 (2000).

[34] S. Okabe, K. Forsberg-Nilsson, A. C. Spiro, M. Segal and R. D. McKay, Development of neuronal precursor cells and functional postmitotic neurons from embryonic stem cells in vitro. Mech Dev 59, 89-102 (1996).

[35] F. Ciccolini and C. N. Svendsen, Fibroblast growth factor 2 (FGF-2) promotes acquisition of epidermal growth factor (EGF) responsiveness in mouse striatal precursor cells: identification of neural precursors responding to both EGF and FGF-2. J Neurosci 18, 7869-7880 (1998).

[36] A. Bignami, L. F. Eng, D. Dahl and C. T. Uyeda, Localization of the glial fibrillary acidic protein in astrocytes by immunofluorescence. Brain Res 43, 429-435 (1972).

[37] V. Tropepe, S. Hitoshi, C. Sirard, T. W. Mak, J. Rossant and K. D. van der, Direct neural fate specification from embryonic stem cells: a primitive mammalian neural stem cell stage acquired through a default mechanism. Neuron 30, 65-78 (2001).

[38] B. A. Reynolds and S. Weiss, Clonal and population analyses demonstrate that an EGF-responsive mammalian embryonic CNS precursor is a stem cell. Dev Biol 175, 1-13 (1996).

[39] S. K. Bronson, E. G. Plaehn, K. D. Kluckman, J. R. Hagaman, N. Maeda and O. Smithies, *Single-copy transgenic mice with chosen-site integration*. Proc Natl Acad Sci USA 93, 9067-9072 (1996).

[40] D. W. Melton, D. S. Konecki, J. Brennand and C. T. Caskey, *Structure, expression, and mutation of the hypoxanthine phosphoribosyltransferase gene*. Proc Natl Acad Sci USA 81, 2147-2151 (1984).

[41] S. Ding, T. Y. Wu, A. Brinker, E. C. Peters, W. Hur, N. S. Gray and P. G. Schultz, *Synthetic small molecules that control stem cell fate*. Proc Natl Acad Sci USA 100, 7632-7637 (2003).

[42] S. Ding and P. G. Schultz, *A role for chemistry in stem cell biology*. Nat Biotechnol 22, 833-840 (2004).

[43] M. Miloso, D. Villa, M. Crimi, S. Galbiati, E. Donzelli, G. Nicolini and G. Tredici, *Retinoic acid-induced neuritogenesis of human neuroblastoma* SH-SY5Y cells is ERK independent and PKC dependent. J Neurosci Res 75, 241-252 (2004).

[44] M. Miloso, A. A. Bertelli, G. Nicolini and G. Tredici, Resveratrol-induced activation of the mitogen-activated protein kinases, ERK1 and ERK2, in human neuroblastoma SH-SY5Y cells. Neurosci Lett 264, 141-144 (1999).

[45] R. W. Stackman, F. Eckenstein, B. Frei, D. Kulhanek, J. Nowlin and J. F. Quinn, Prevention of age-related spatial memory deficits in a transgenic mouse model of Alzheimer's disease by chronic *Ginkgo biloba* treatment. Exp Neurol 184, 510-520 (2003).

[46] B. Ahlemeyer and J. Krieglstein, *Neuroprotective effects of Ginkgo biloba extract*. Cell Mol Life Sci 60, 1779-1792 (2003).

[47] M. Yamazaki, K. Hirota, K. Chiba and T. Mohri, *Promotion of neuronal differentiation of PC12h cells by natural lignans and iridoids*. Biol Pharm Bull 17, 1604-1608 (1994).

[48] Y. Jing, S. Nakajo, L. Xia, K. Nakaya, Q. Fang, S. Waxman and R. Han, *Boswellic acid acetate induces differentiation and apoptosis in leukemia cell lines*. Leuk Res 23, 43-50 (1999).

[49] A. Mahonen, T. Jaaskelainen and P. H. Maenpaa, A novel vitamin D analog with two double bonds in its side chain. A potent inducer of osteoblastic cell differentiation. Biochem Pharmacol 51, 887-892 (1996).

[50] T. Takahashi, B. Lord, P. C. Schulze, R. M. Fryer, S. S. Sarang, S. R. Gullans and R. T. Lee, *Ascorbic acid enhances differentiation of embryonic stem cells into cardiac myocytes*. Circulation 107, 1912-1916 (2003).

[51] T. Uetsuki, K. Takagi, H. Sugiura and K. Yoshikawa, Structure and expression of the mouse necdin gene. Identification of a postmitotic neuron-restrictive core promoter. J Biol Chem 271, 918-924 (1996).

[52] A. Gloster, W. Wu, A. Speelman, S. Weiss, C. Causing, C. Pozniak, B. Reynolds, E. Chang, J. G. Toma and F. D. Miller, The T alpha 1 alpha-tubulin promoter specifies gene expression as a function of neuronal growth and regeneration in transgenic mice. J Neurosci 14, 7319-7330 (1994).

[53] K. Shimoda, H. Ikeshima, K. Matsuo, J. Hata, K. Maejima and T. Takano, Spatial and temporal regulation of the rat calmodulin gene III directed by a 877-base promoter and 103-base leader segment in the mature and embryonal central nervous system of transgenic mice. Brain Res Mol Brain Res 31, 61-70 (1995).

[54] K. Makinae, T. Kobayashi, T. Kobayashi, H. Shinkawa, H. Sakagami, H. Kondo, F. Tashiro, J. Miyazaki, K. Obata, S. Tamura and Y. Yanagawa, *Structure of the mouse glutamate decarboxylase 65 gene and its promoter: preferential expression of its promoter in the GABAergic neurons of transgenic mice*. J Neurochem 75, 1429-1437 (2000).

[55] J. R. Shaw-White, N. Denko, L. Albers, T. C. Doetschman and J. R. Stringer, *Expression of the lacZ gene* targeted to the HPRT locus in embryonic stem cells and their derivatives. Transgenic Res 2, 1-13 (1993).

[56] I. Vicario and T. Schimmang, Transfer of FGF-2 via HSV-1-based amplicon vectors promotes efficient formation of neurons from embryonic stem cells. J Neurosci Methods 123, 55-60 (2003).

[57] S. Chiba, M. S. Kurokawa, H. Yoshikawa, R. Ikeda, M. Takeno, M. Tadokoro, H. Sekino, T. Hashimoto and N. Suzuki, Noggin and basic FGF were implicated in forebrain fate and caudal fate, respectively, of the neural tube-like structures emerging in mouse ES cell culture. Exp Brain Res 163, 86-99 (2005).

[58] J. W. McDonald, X. Z. Liu, Y. Qu, S. Liu, S. K. Mickey, D. Turetsky, D. I. Gottlieb and D. W. Choi, *Transplanted embryonic stem cells survive, differentiate and promote recovery in injured rat spinal cord*. Nat Med 5, 1410-1412 (1999).

[59] C. B. Harley and M. S. Rao, *Human Embryonic vs Adult Stem Cells for Transplantation Therapies*. In Human Embryonic Stem Cells. (Ed. A. Y. Chiu and M. S. Rao) p. 239264, Humana Press Inc., 2003.

[60] B. R. Clark, M. LaRegina and D. L. Tolbert, X-linked transmission of the shaker mutation in rats with hereditary Purkinje cell degeneration and ataxia. Brain Res 858, 264-273 (2000).

[61] D. L. Tolbert and J. Heckroth, Purkinje cell transplants in Shaker mutant rats with hereditary Purkinje cell degeneration and ataxia. Exp Neurol 153, 255-267 (1998).

[62] G. M. Kim, J. Xu, J. Xu, S. K. Song, P. Yan, G. Ku, X. M. Xu and C. Y. Hsu, Tumor necrosis factor receptor deletion reduces nuclear factor-kappaB activation, cellular inhibitor of apoptosis protein 2 expression, and functional recovery after traumatic spinal cord injury. J Neurosci 21, 6617-6625 (2001).

[63] M. X. Doss, C. I. Koehler, C. Gissel, J. Hescheler and A. Sachinidis, *Embryonic stem cells: a promising tool for cell replacement therapy*. J Cell Mol Med 8, 465-473 (2004).

[64] J. H. Kim, J. M. Auerbach, J. A. Rodriguez-Gomez, I. Velasco, D. Gavin, N. Lumelsky, S. H. Lee, J. Nguyen, R. Sanchez-Pernaute, K. Bankiewicz and R. McKay, *Dopamine neurons derived from embryonic stem cells function in an animal model of Parkinson's disease*. Nature 418, 50-56 (2002).

[65] D. M. Yurek and A. Fletcher-Turner, Comparison of embryonic stem cell-derived dopamine neuron grafts and fetal ventral mesencephalic tissue grafts: morphology and function. Cell Transplant 13, 295-306 (2004).

[66] E. Genschow, H. Spielmann, G. Scholz, A. Seiler, N. Brown, A. Piersma, M. Brady, N. Clemann, H. Huuskonen, F. Paillard, S. Bremer and K. Becker, *The ECVAM international validation study on in vitro embryotoxicity tests: results of the definitive phase and evaluation of prediction models. European Centre for the Validation of Alternative Methods*. Altern Lab Anim 30, 151-176 (2002).

[67] A. Seiler, A. Visan, R. Buesen, E. Genschow and H. Spielmann, Improvement of an in vitro stem cell assay for developmental toxicity: the use of molecular endpoints in the embryonic stem cell test. Reprod Toxicol 18, 231-240 (2004).

SUMMARY OF THE INVENTION

The inventor has developed a method for generating embryoid bodies of a uniform size, which lend themselves to the medium and high through-put screening of agents that affect development and physiology. The method enables the development of those screens by easily producing at least one embryoid body (and preferably one embryoid body) per well in a multiwell format.

Thus, an object of the invention is a method for producing from one to five embryoid bodies per vessel, wherein each embryoid body has a uniform size relative to other embryoid bodies. Preferably, the uniform size is from 300 microns to 600 microns in diameter. More preferably, the uniform size is about 400 microns±20%. Most preferably, the uniform size is about 415 microns±10%. The method comprises (a) genetically modifying an embryonic stem cell to contain a reporter gene and selectable marker gene operably linked to a developmentally regulated promoter, (b) growing the ES cells in the presence of feeder cells, (c) predifferentiating the ES cells by removing the feeder cells, (d) dissociating the ES cells and culturing them in differentiation media, (e) placing approximately 1,000 ES cells into a single vessel in 200 uL of media, which gives rise to an EB having an average diameter of 415 nm±10%.

Another object of the invention is an EB having a uniform size and comprising ES cells containing a reporter gene and selectable marker gene operably linked to a developmentally regulated promoter. Preferably, the uniform size is from 300 microns to 600 microns in diameter. More preferably, the uniform size is about 400 microns±20%. Most preferably, the uniform size is about 415 microns±10%. Exemplary developmentally regulated promoters are set forth in Table 1 (supra). Preferred reporter genes are well known in the art, such as the lacZ gene, green fluorescent protein and variants thereof, and luciferase.

Another object of the invention is a kit for screening agents that affect the development or homeostasis of a developing or developed organism. The kit comprises a plurality of embryoid bodies distributed across a multiplex format, such as a 96-well plate (or any such multiwell plate format). The EBs are formed as herein described (infra and supra). In a preferred embodiment, there is one EB per well of the multiwell format. External agents are applied to the multiwell plate (or other format) to determine the effect on homeostasis and/or development. Preferably, in the multiwell format, there is no more that five EBs per well. Most preferably, there is one EB per well. The EB comprises engineered ES cells (as herein disclosed). Each EB has a uniform size as herein described.

Another object of the invention is a method for screening agents for an effect on development or homeostasis of a developing or developed organism. The method comprises (1) contacting a plurality of uniform embryoid bodies with an agent to be tested, (2) waiting a specified amount of time, (3) assessing the status of gene expression and/or developmental phenotype of the embryoid body, and (4) determining the effect of the agent on the development and/or homeostasis of the embryoid body, and (5) assigning an attribute to the agent, wherein the attribute is whether the agent is toxic, non-toxic, morphogenic, non-morphogenic, therapeutic, et cetera. A preferred reporter is lacZ or luciferase reporter. A preferred selection marker is a puromycin or hygromycin selection marker. In a preferred embodiment, the reporter and selection markers are under the control of a specific promoter in the form of a promoter-selection-reporter cassette (supra).

BRIEF DESCRIPTIONS OF THE DRAWINGS

FIG. 1 depicts embryoid bodies. Panel A: Embryonic stem ("ES") cells differentiated into embryoid bodies; panel B: embryoid body formed from ES cell line expressing necdin-beta galactosidase; the stained areas represent cells expressing beta-galactosidase.

FIG. 2 depicts the various vector contructs used in ES cell transfection. Panel A: plasmid pUT2 with multiple; panel B: plasmid PILPN; panel C: vector UPN; panel D: pHPRT targeting vector; panel E is a map of the mouse HPRT genomic locus. Abbreviations for restriction sites are A=Acc651, B=BamH1, E=EcoR1, V=EcoRV, H=HindIII, S=Sac1 and X=Xba1.

FIG. 3 depicts ES cells differentiating into neurons on day 12. Panel A: indirect immunofluorescence with antibody against neuron cytoskeletal protein MAP2; Panel B: same field as in A, bright field; Panel C: same field as in A, DAPI staining (nuclei).

FIG. 4 depicts necdin promoter-driven lac Z. Panel A: After 12 hours of differentiation showing positive staining; Panel B: same field as in A, DAPI staining (nuclei).

FIG. 5 depicts the presence of neurons on day 16 after puromycin selection. Panel A: indirect immunofluorescence with antibody against neuron cytoskeletal protein MAP2; Panel B: same field as in A, bright field; Panel C: indirect immunofluorescence with antibody against low affinity NGF receptor; Panel D: same field as in C, bright field.

Figure 10:
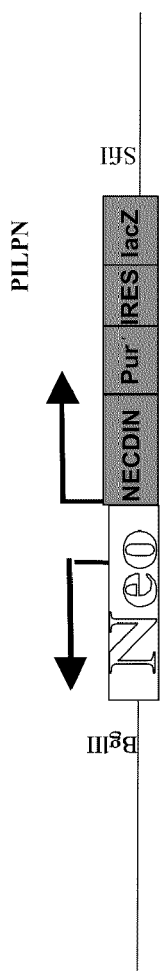

FIG. 10. Distribution of a single EB into a microwell. Results are from three independent experiments labeled A, B and C. For each experiment, individual EB sizes were measured in microns using phase contrast microscopy. Results are displayed as mean micron size±SEM. n=number of EB assessed for size measurements. No significant difference exists amongst the three groups. Experiment A: 428±14, n=20. Experiment B: 427±14, n=20. Experiment C: 392±11, n=17.

Figure 11:
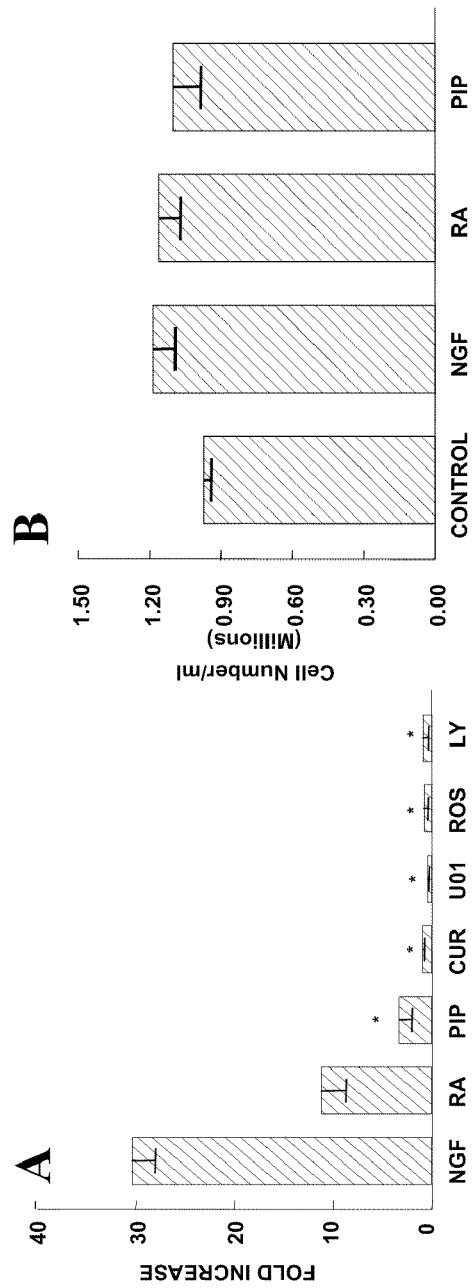

FIG. 11. Formation of EB in a 96 well format polycarbonate PCR plate. On average, 94% of the wells from four independent experiments contained single EB. Results displayed in A and B are phase contrast microscopy using the same magnification A. Microwell containing a single EB of typical size. B. Microwell containing two EB of dissimilar sizes and size dissimilar from the single EB. Arrows point to the EB.

DETAILED DESCRIPTION OF THE INVENTION

An object of the invention is a plurality of engineered embryoid bodies (EBs), such that each embryoid body is of a relative uniform size, which are useful in the screening of various agents that may have an effect on the development and/or physiology of a complex organism. In a preferred embodiment, each engineered embryoid body comprises a recombinant polynucleotide containing a cell-type specific promoter (such as for example a neuron-specific promoter) driving the expression of a reporter gene (such as for example lacZ or luciferase) and one or more selection markers (such as for example puromycin-resistance marker and/or hygromycin-resistance marker). The strategy is that reporter and selection marker genes are expressed only in lineages where the promoter is functional and that small molecules will inhibit, augment or have no effect on cell lineage differentiation. The differentiated cell type is identified by analysis of reporter gene expression and the importance of the selection marker is selective enrichment of that particular cell population. Through the creation of a panel of lineage-specific promoter-reporter embryonic stem (ES) cell lines, screening of EB from these cell lines provides an excellent system for testing differentiation effects of agents (e.g., small molecules). Information gleaned from this panel is useful in determining whether a particular agent is a modulator of development of a particular cell lineage (a.k.a. morphogen). Differentiation of ES cells into different cell lineages is of great importance since the potential exists for application of discovered technologies as therapeutics for regenerative medicine. If an agent has the potential to drive the EB into development of a specific cell lineage, then this small molecule is considered a valuable reagent and potential therapeutic.

The following non-limiting exemplary screening technologies are applicable to the use of single, uniform-sized EBs grown in a multi-well format: (1) a model to screen for infectious biological agents, (2) a model system to screen for compounds that inhibit infectious agents, (3) a model system to screen small molecules and compounds that potentiate or inhibit generation of particular lineages of cells, (4) a model system to screen for toxic molecules, (5) a model system for inhibition or interference of EB formation.

EB as a Model to Screen for Infectious Biological Agents

The availability of a cell culture system that models the life cycle of an infectious agent, as well as to study its effect on host cell physiology, provides a powerful tool with which to screen for, diagnose and understand the mechanisms of action of an infectious agent at the molecular level. EBs recapitulate the embryonic development of all cell types thereby making it an ideal system to assess infectivity. For example, nucleic acid-containing viruses and protein infectious agents such as prions can be mixed with ES cells and then allowed to form single, uniform-sized EBs in a multi-well format. A trophic virus, or any virus for that matter, infects the cell type(s) and replicate. After certain time points, EBs will have sufficient numbers of infective particles detectable by commonly used assays such as for example enzyme-linked immunosorbent assays (ELISA). Either the EB in the multi-well format can be lysed to quantitate number of cell bound virion particles, or the supernatant can be assayed for the quantitation of released infectious agents. This technique using EB allows the screening of infectious agents not normally detectable by current methods and allows for detection of infectious agents in an in vivo model organism. Alternatively, if an infectious agent from another species requires a particular receptor or a protein product to be present, then the ES cell can be genetically modified such that cross-species screening can be performed. An example is an infectious prion protein (PrPsc). Much is known about interactions of prions with organ systems and cells in animal models for genetic as well as transmissible spongiform encephalopathies (TSE). The ability to use a carefully characterized culture system in which to study the molecular details of prion infection provides the potential for significant advances in our understanding of these unconventional infectious agents. The current methods of prion assessment rely on the detection of total prion-related protein, not on the detection of the infectious agent itself. In the cattle industry, detection of bovine spongiform encephalopathy (BSE) is by random selection of animals for slaughter or euthanasia of a downer cow followed by the harvest of brain tissue and subsequent assessment of extracts of the tissue for the presence of prion proteins. Even though there are five companies marketing kits that detect disease-causing prion proteins ($PrP^{Sc}$) from tissue samples (21), there are currently no commercial kits available that detect the infectious prion protein in a timely and cost-effective manner.

Figure 2:
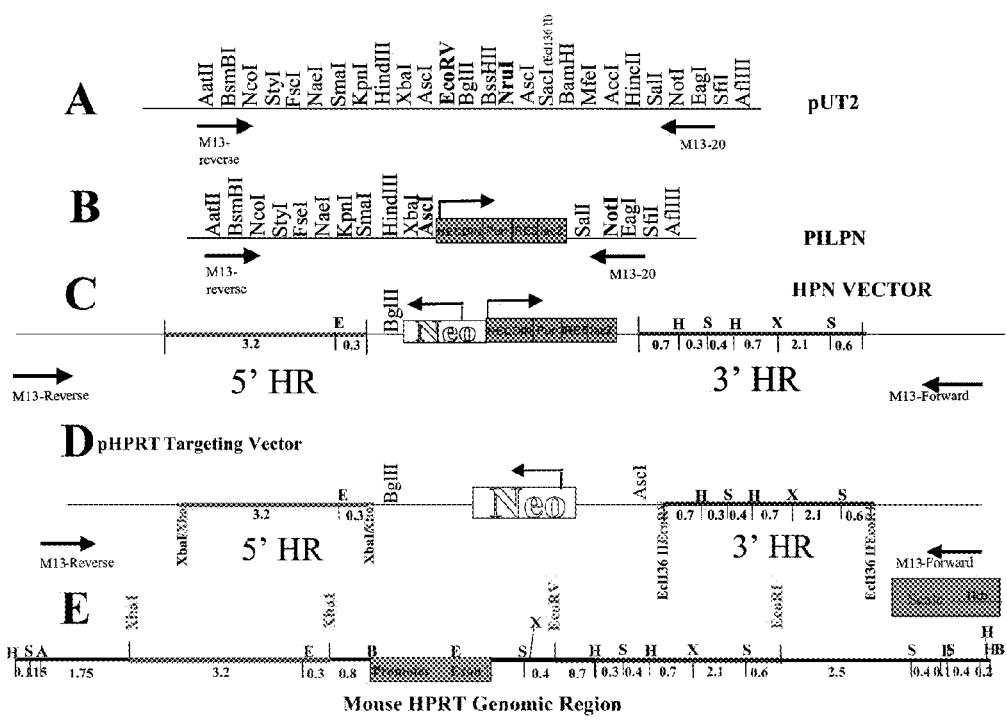

The only method of positive identification of prion infection is by animal testing as demonstrated in mouse models where the infectious agent, after inoculation into mice, has taken 150 days to show symptoms. This method requires a lengthy time period to obtain results thereby making it cumbersome and with little direct applicability to the clinical setting. For example, ES cells containing suspect $PrP^{Sc}$ from a population sample when cultured in a multi-well format may show positivity which would have been reported as negative by conventional methodology. The ES cells form EBs which contain trapped $PrP^{Sc}$. Addition of retinoic acid to this culture at appropriate time points allows the EB to have more cells differentiating along a neuronal pathway. After certain time points, the $PrP^{Sc}$ infects the developing neurons thereby creating more infectious particles. The EB are then lysed for assessment by ELISA for the presence of PrPSc. Another advantage is that respective gene(s) which are the signposts for particular species can be placed in mouse (or any mammal, such as human) ES cells and used as a model system. Extension of this technique is detection of prions from other species by the replacement of the mouse PrP gene with those from other species such as the bovine or human PrP gene thus allowing in vitro testing to detect the infectious agents of transmissible spongiform encephalopathies such as BSE ("Mad Cow Disease") and CJD or vCJD (the genetic and infectious forms of Creutzfeldt-Jakob Disease). Another useful extension is the creation of ES cells in which both copies of the PrP gene is "knocked out" as a universal negative control for this assay. The advantage is less cost and the screening time can be reduced to few weeks time rather than months as in the in vivo model, EB as a Model System to Screen for Compounds that Inhibit Infectious Agents ES cells are genetically modified so that they express a viral specific promoter and/or a specific promoter which is induced several fold upon viral infection that drives a reporter gene such as luciferase, green fluorescent protein (GFP), and/or beta-galactosidase in a particular cell type upon infection by a particular agent. The expression of the reporter is useful to measure the infectivity of the agent and to identify compounds that thwart the expression of the infectious agent thereby being indicative of an anti-infectious effect of the compound. Genetically-engineered ES cells are allowed to form EB and at appropriate time points when the EB express the cell type of interest, the infectious agent (with and without screening compound [agent]) is added. Measurement of the reporter of the infectious agent alone ise the positive control. Any reduction in the reporter expression is indicative of the ability of the compound (agent) to inhibit infectious agent reproduction.

EBs as Model System to Screen Agents that Modulate Generation of Specific Cell Lineages The in vitro differentiation potential of ES cells allows their use as a model system for the study of developmental potential and also as a valuable reagent for stem cell therapeutic approaches. ES cells differentiated into different cell types are useful in regenerative medicine; however, a caveat for this application of ES cells is the ability to obtain sufficient quantity of high purity lineages of specific cell types. Since differentiation of ES cells into various lineages is a highly studied area because of direct applicability to regenerative medicine, a screening method capable of identifying agents that drive ES cell differentiation along particular lineages is of great interest. Identification of agents as regulators of cell type-specific ES cell differentiation provides powerful tools in the emerging area of regenerative medicine. Many aspects of the lineage-specific differentiation programs observed within embryoid bodies indicate that embryoid bodies reflect cells found in the complete embryo, thereby indicating that this model system provides access to early cell populations that develop in a normal fashion. By creation of a panel of lineage-specific promoter-reporter ES cell lines, screening of EB from these cell lines provides an excellent system for testing differentiation effects of agents. These agents may have either no effect, or may increase or decrease the differentiation potential of specific cell types desired. Additionally, tissue specific promoters (see for example those promoters listed in Table 1) may be used to express selection markers with the reason being that if a "hit" compound drives the ES cell along a particular differentiation lineage, then the obtained lineage may be further characterized. Upon application of the selection agent, only the "hit" compound, which is the agent that induced the differentiated population, allows the survival of that particular lineage and the elimination of "undesired" cell types. What follows is a non-limiting example of use of this technique to allow selection of the exemplary neuronal cell type. Briefly, the targeting vector contains a neuron-specific promoter (in which the core promoter specifies expression only in post-mitotic neurons; e.g., necdin promoter) that drives the expression of an exemplary selection marker (puromycin) and an exemplary reporter (lacZ). The plasmid construct has an internal ribosomal entry site (IRES) that allows the co-translation of both the selection gene and the reporter gene. The plasmid also contains a Neo selection marker driven by a PGK promoter. Transcription of PGK and necdin genes is designed to be opposite in orientation (see plasmid PILPN, FIG. 1). Digestion of the PILPN vector with SfiI linearizes PILPN so the plasmid readily electroporates into ES cells which then can be plated onto tissue culture dishes. ES cells are then cultured onto an embryonic fibroblast feeder layer at 37° C. and 7.5% $CO_2$ in standard ES cell culture media containing leukocyte inhibitory factor (LIF). After 24 h incubation, G418 selection can be performed by addition of ES cell media containing G418 (400 μg/ml) to the cells that are then allowed to grow for 5 days. Only cells transfected with plasmid survive in the presence of G418 Surviving colonies are picked, expanded and analyzed for the presence of lacZ and puromycin genes by PCR analysis.

A single colony was chosen to demonstrate the screening for neurogenesis. A brief description of the procedure follows. A tagged ES cell line containing a stably integrated necdin-puromycin-IRES-β-galactosidase cassette was allowed to form EBs. One thousand cells in 200 μl media without LIF were plated in a 96-well PCR plate. On the third day, the EBs were transferred to a 96-well tissue culture plate coated with laminin. The medium was changed on the fourth day and appropriate small molecule compounds were added with each compound being assessed in triplicate. Six wells received no treatment and six wells received treatment with vehicle control (DMSO or ethanol diluted in similar manner as small molecule compounds). The cells were incubated with compounds for 48 hours, compounds removed by washing with PBS and cells allowed to grow and differentiate in media for 4 days. Cells were lysed on the fifth day and the lysates were analyzed for β-galactosidase expression. FIG. 2A shows the effects of the indicated compounds at 10 μM concentrations. Two positive controls, 50 ng/ml nerve growth factor (NGF) and 1 uM retinoic acid (RA) (Sigma Chemical, St. Louis) and small molecule compounds (piperine, curcumin, rosmarinic acid, U0126, LY294002) were used for screening. Fold increase was calculated based on the respective vehicle control β3-galactosidase activity. NGF showed more (30-fold) neurogenesis than did RA (11-fold). This is not surprising since NGF is a stronger neurogenic growth factor than is RA. Piperine had a 3.3-fold increase for neurogenesis but this was not significantly different statistically from the control. However, since the test compounds did not display increases equal to or greater than the controls (NGF or RA), a reasonable interpretation of this throughput screen is that none of these small molecules have neurogenesis potential. The piperine-induced 3.3-fold increase for neurogenesis may be due to induction of cell division; however, no significant increase in cell number was observed (FIG. 2B). These combined results demonstrate that NGF, RA and piperine effects are on neurogenesis and not on cell division. As a reminder, in this developed screen assay, compounds are defined as "hits" only if they show equal or greater results than the positive (NGF or RA) controls. The differentiation of ES cells into various lineages is a highly studied area largely because of the direct applicability of ES cells into the field of regenerative medicine. If a small molecule has the potential to drive EB into a specific neuronal lineage of cells, then it will be a valuable reagent. Such "hit" molecules will be of importance because of their great therapeutic potential in treating various types of neuronal degenerative diseases, such as Parkinson's disease, motor neuron degeneration, amyotrophic lateral sclerosis, stroke and spinal cord injury.

Example 1

Construction of Vectors

Construction of HPRT Targeting Vector

FIG. 2E is a map of the mouse HPRT genomic locus. The promoter and exon 1 of the HPRT gene is in the central region and designated by the box. The pUT1 vector backbone was used to construct the targeting vector. To make the targeting vector (FIGS. 2D and 2E), the 5' and 3' homologous regions flanking the 5' region of the promoter and the 3' region of exon 1 were used. Transcription of the HPRT gene requires the promoter region. The targeting vector was designed such that homologous recombination of this vector at the HPRT locus eliminates the promoter-exon 1 region thereby completely eliminating HPRT gene expression. The strategy utilized for construction of the HPRT targeting vector follows. Plasmid pUT1 was used as a backbone to engineer the targeting vector. The source of the HPRT gene was a BAC clone identified by screening a BAC library made from 129/SvJ mouse genomic DNA. The BAC DNA was subcloned and relevant genomic regions were used to construct the HPRT targeting vector. The targeting vector was constructed from the 3.5 Kb Xba1 DNA fragment located in the 5' upstream region of the promoter and from a 4.8 Kb EcoRV and EcoRI DNA fragment located in the 3' region downstream of exon 1 (FIGS. 2D and 2E). The 5' Xba1 fragment was cloned into a pUT1 plasmid at the Xba1 site and 3' DNA fragment EcoRV-EcoRI subjected to a fill-in reaction and cloned at the Ecl136II site that created a blunt end. At the EcoRV site of pUT1 containing 5' and 3' arms, a Neo$^r$ selection gene was cloned. The presence of the phosphoglycerate kinase (Pgk) promoter allows for constitutive expression of the Neo$^r$ gene. Addition of the antibiotic G418 to cells containing a Neo$^r$ marker blocks protein synthesis by inhibition of ribosomal function. Cells expressing the Neo$^r$ marker survive when grown in the presence of G418 because the Neo$^r$ gene causes detoxification of G418 thereby allowing for cell growth.

Construction of Targeting Vector with Neuron Specific Promoter

Two modified pUC19 plasmids were made and used as the backbone for target vector construction. Plasmid pUC19 was digested by AatII and AflII restriction enzymes. This digestion produced two DNA fragments: 0.875 Kb which contains the polylinker cloning site and the lacZ gene of pUC19; and 1.81 Kb which contains the β-lactamase gene and the origin of replication. To the 1.81 Kb DNA fragment, several restriction sites were added by sequential ligation of oligolinkers thereby creating plasmid pUT1 and pUT2. (FIG. 2A). According to Uetsuki et al [51], an 844 bp DNA fragment upstream of the transcription initiation start site for the necdin gene contains promoter activity in differentiated neuronal cells. The necdin gene is expressed in all post-mitotic neurons [21, 23]. For the present study, the necdin promoter region was cloned from a mouse genomic DNA by polymerase chain reaction (PCR) amplification of a 951 bp of DNA fragment upstream of the translation initiation site. The primers for necdin amplification were chosen from the mouse necdin sequence available from GenBank (accession number D76440). The forward primer corresponded to nucleotide numbers 1-26 of that mouse necdin sequence and the reverse primer corresponded to nucleotide numbers 956-937 of that mouse necdin sequence. A PCR reaction was done using Pwo DNA polymerase (Roche Applied Science, Indianapolis, Ind.) and the PCR amplification reaction was performed according to manufacturer's guidelines. The amplified DNA fragment was cloned into the NruI/EcoRV site of the pUT2 vector (FIG. 2A). The cloned necdin promoter was verified by sequencing of the region and by restriction enzyme digestion: the plasmid containing the necdin promoter was named pNecdin. As a first step, the IRES DNA fragment with the multiple cloning site (MCS) from pIRES (Clontech, Palo Alto, Calif.) was cloned into a pUT2 plasmid vector. The pIRES plasmid was digested with PstI followed by a T4 DNA polymerase reaction to create blunt ends. This DNA molecule was digested with SalI and gel purified. The resultant 899 bp nucleotide fragment containing IRES and MCS was cloned into pUT2 at NruI and SalI sites and this plasmid was called PGIRES. In the second step, SmaI and SalI digestion of a pCMV beta vector (Clontech) gave a 3.6 kb β-galactosidase DNA fragment (reporter gene) which was cloned into a BamH1 site blunt-ended by a T4 DNA polymerase reaction and a SalI site. The resulting plasmid was called PIL. In the third step the DNA fragment containing the puromycin resistance gene (puromycin-N-acetyl-transferase gene or Pur$^r$ from pPUR vector [Clontech]) was cloned into the PIL vector. The DNA fragment harboring Pur$^r$ was isolated by digestion with AvrII and MfeI restriction enzymes. The isolated 919 bp DNA fragment was cloned into PGIRES at NheI and EcoRI I sites. The resulting plasmid was called PILP. In the fourth step, the necdin promoter was isolated from a pNecdin vector by digestion with AscI and Ecl136 and the resulting DNA fragment was cloned into the AscI-EcoRV site of PILP. The plasmid was called PILPN (FIG. 2B). To make the HPRT vector containing the necdin promoter-selection-IRES-reporter cassette, the PILPN vector was digested with SfiI followed by a T4 DNA polymerase reaction to create blunt ends. This blunt-ended DNA fragment was digested by AscI and cloned into AscI and EcoRV sites of the HPRT vector. The resulting vector was called HPN (FIG. 2C).

Example 2

Development of ES Cell Lines

Transfection of ES Cells with the HPRT Targeting Vector

ES cells were electroporated (180 V, 500 uF) with 10 μg linearized HPRT targeting vector (FIG. 2D). After electroporation, ES cells were cultured on a fibroblast feeder layer at 37° C. and 7.5% $CO_2$ in standard ES cell culture media of Dulbecco's minimal essential medium with high glucose, L-glutamine (DMEM: Invitrogen, Carlsbad, Calif.) plus 1 mM sodium pyruvate, 10% fetal calf serum, 100 μM β-mercaptoethanol and 1000 U/ml LIF (ESGRO®, Chemicon). After 24 h, G418 selection was performed by G418 (400 μg/ml) addition and the cells were allowed to grow for 5 days. Only cells transfected with the HPRT targeting vector survived in the presence of G418. After 5 days, 30 μM 6-TG was added to the standard ES cell culture media and cells were grown for 7-10 days. Only cells with a mutated HPRT gene grew in 6-TG.

Selection of Cells Containing the Targeted IPRT Gene

Figure 8:
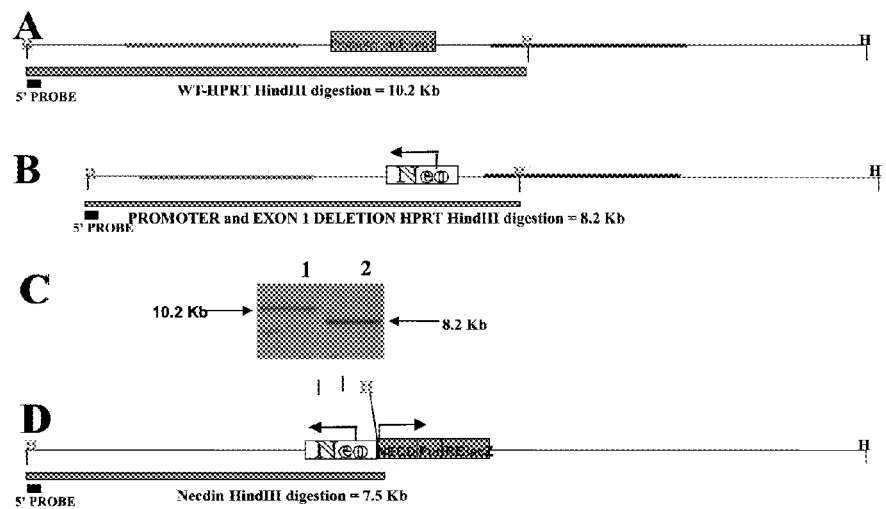
FIG. 8 depicts a screening strategy for targeting HPRT. Panel A: HindIII digestion of control genomic DNA produces 10.2 kb fragment; panel B: HindIII digestion of pHPRT genomic DNA produces 8.2 kb fragment; panel C: genomic souther; panel D: promoter-selection-reporter cassette cloned into pHPRT vector.

To identify that the mutation in the HPRT gene was due to gene targeting, a Southern blot was performed to verify that a homologous recombination event occurred. After 8-10 days, surviving colonies were picked and grown in 0.1% gelatin-coated 24-well plates without 6-TG but in the presence of G418. When the cells reached confluence, genomic DNA was isolated using a standard protocol [11, 28]. A 5' probe was made by PCR amplification of the 200 by DNA fragment from the region between HindIII and Acc65I. This probe is depicted as a black box on the 5' end of FIGS. 8 A, B and C. FIG. 8 shows the screening strategy for the targeting event. The 5' probe was labeled with deoxycytidine 5'-[$\alpha$-$^{32}$P] triphosphate and Rediprime® II DNA labeling system (Amersham, Piscataway, N.J.). Genomic DNA was digested with HindIII and electrophoresed on an agarose gel and blotted onto a nylon membrane followed by hybridization with the labeled 5' probe (FIG. 8). As depicted by the box under the HPRT map (FIG. 8A), HindIII digestion of wild type genomic DNA produced a fragment of 10.2 Kb size by Southern blot using the 5' labeled probe (FIG. 8C, lane 1). The targeted HPRT region has a deletion of the promoter-exon 1 region (4 Kb) and a replacement of a Neo$^r$ selection marker cassette (~2 Kb size). Therefore, HindIII digestion of the targeted HPRT gene resulted in an 8.2 Kb DNA fragment (FIG. 8C, lane 2). A Southern blot using a probe specific for the neomycin region resulted in the same size band (8.2 Kb) in genomic DNA from targeted cells. This result is essential because a random integration event would show more than a single band. From a total of 15 colonies obtained, 12 had the correct targeting result based upon the use of the 5' and neomycin probes and Southern analysis. These results show that 6-TG selection is a powerful method for the identification of HPRT targeting events.

ES Cell Line Expressing Necdin Promoter-Reporter-Selection Cassette

Figure 1:
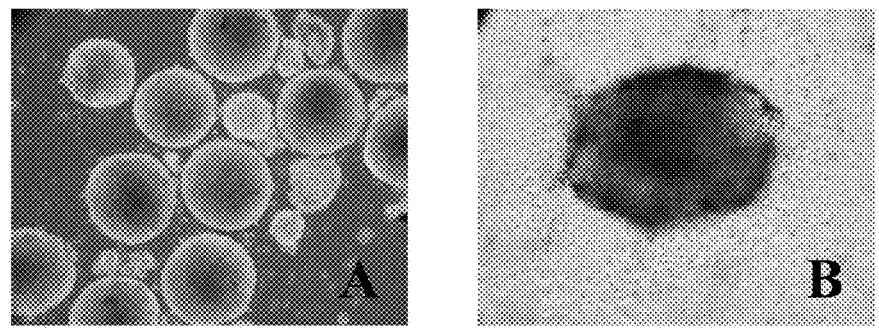
Figure 3:
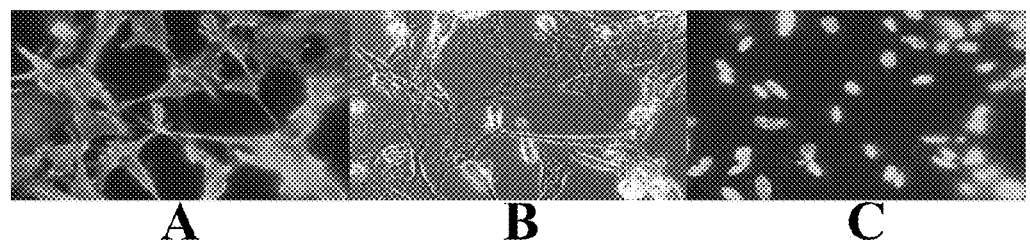
Figure 4:
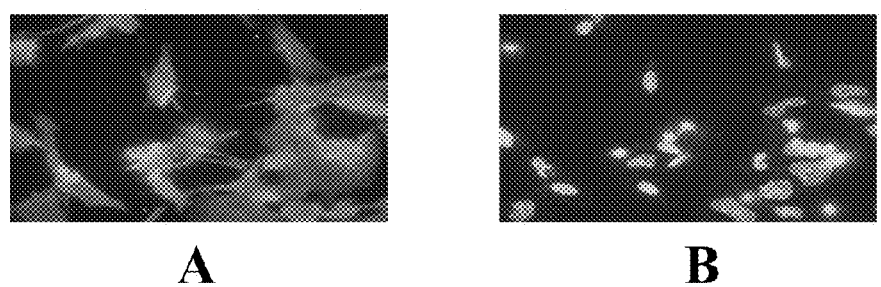
Figure 5:
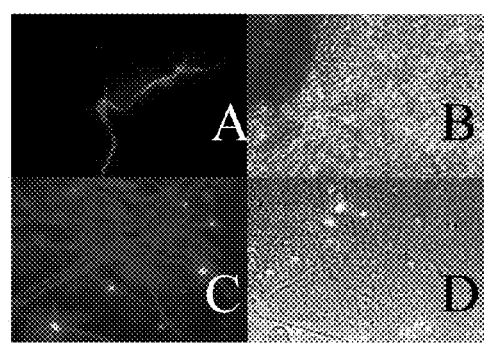
Figure 6:
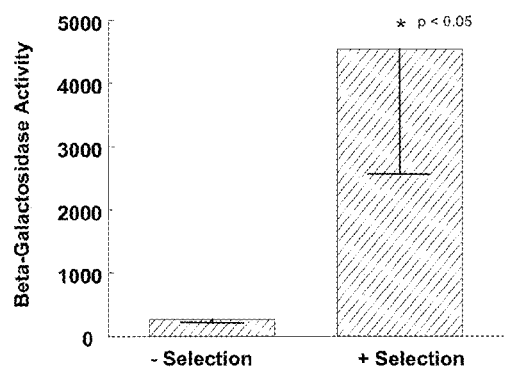
FIG. 6 depicts puromycin selection at day 12. Panel A: Beta-gal activity; panel B: cell counts of cells stained with MAP2 for neurons and GFAP for astrocytes.
Figure 6:
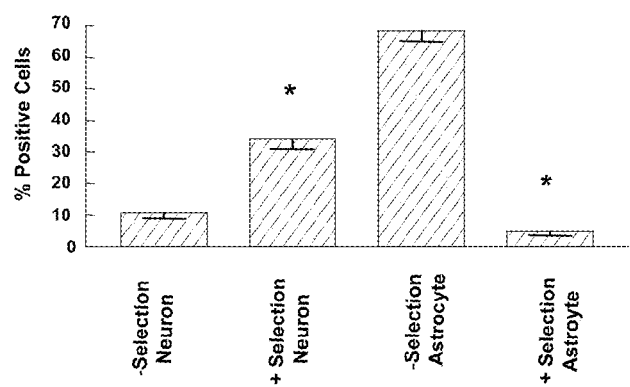
Figure 7:
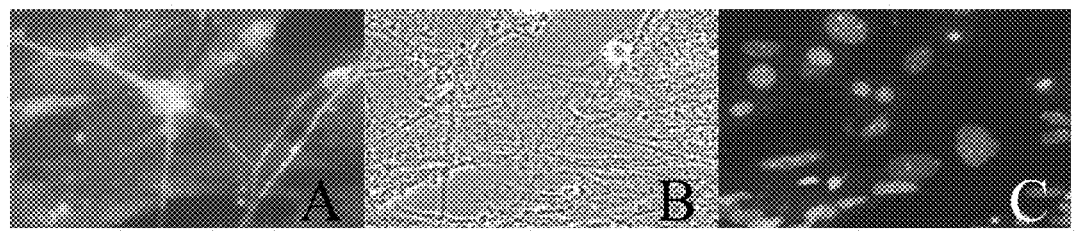
FIG. 7 depicts the expression of beta-gal from the necdin promoter at day 12. Panel A: double staining for beta-gal and low affinity NGF receptor; panel B:m same field as A, bright field; panel C: field as in A, DAPI staining (nuclei).

The PILPN targeting vector was digested with SfiI. A plasmid containing a neomycin (Neo) cassette was linearized by digesting with NotI. The linearized PILPN and Neo cassette were co-electroporated into ES cells. The electroporated cells were plated onto tissue culture dishes. Briefly, ES cells were cultured on an embryonic fibroblast feeder layer at 37° C. and 7.5% $CO_2$ in standard ES cell culture media containing LIF. After 24 h, G418 selection was performed by addition of ES cell media containing G418 (400 μg/ml) and cells was allowed to grow for 5 days. Only cells transfected with plasmid survived in the presence of G418 The surviving colonies were picked and expanded and analyzed for the presence of lacZ and puromycin genes by PCR analysis. Six colonies were positive and clone number 6 (ES-6) was chosen for further studies. ES cells differentiated into neurons were characterized by immunocytochemistry. FIG. 1B shows the lacZ staining of the EB indicating the presence of cells expressing β-galactosidase under the necdin promoter. FIGS. 3 and 7 provide examples of ES cells differentiated with RA into neurons which stain positive for MAP2 and the low affinity NGF receptor and have a typical neuronal morphology. Neuronal cells present on day 12 of differentiation also express β-galactosidase as determined by indirect immunofluorescence with anti-β-galactosidase antibody (Roche) followed by Oregon Green conjugated secondary antibody (Molecular Probes, Eugene, Oreg.) (FIG. 4). This result indicates that the necdin promoter drives expression of the lacZ gene and that the necdin promoter is active in differentiated neuronal cell types. To demonstrate that the selection procedure enriches for neurons, ES-6 was plated in Petri dishes to form EB and after 4 days, EB were exposed to RA (1 μM) for another 4 days which constitutes the $4^-/4^+$ protocol [4, 32]. On day 9, EB were trypsinized and plated onto laminin coated tissue culture dishes and this was termed day 1 of differentiation. On day 4 of differentiation, one set of cells received puromycin for 3 days to enrich for neuron selection and another set received no selection pressure (control). The selection drug puromycin was removed on day 7 and culture media was added to the plates. After days 10, 12 and 16, cells grown in the presence or absence of puromycin were analyzed for neuron enrichment (FIGS. 5 and 6). FIG. 7 shows double immunostaining for β-galactosidase and a neuronal marker, the low affinity NGF receptor. The neurons were stained for both markers indicating neuronal expression of the β-galactosidase reporter. Since the necdin promoter confers β-galactosidase expression, a quantitative measurement of β-galactosidase activity was performed with and without puromycin selection. FIG. 6A shows results of cells on day 12 of differentiation. With selection, enrichment of neurons occurs compared to no selection. Immunocytochemistry analysis was done to confirm the biochemical data obtained from beta galactosidase activity. Day 12 differentiated cells with and without selection were stained with MAP2(a+b) antibody as a marker for neurons and with GFAP antibody for astrocytes. Selection enriched for neurons and not for a non-neuronal cell type, astrocytes (FIG. 6B).

Example 3

Effect of Small Molecules on ES Cell Differentiation

Figure 9:
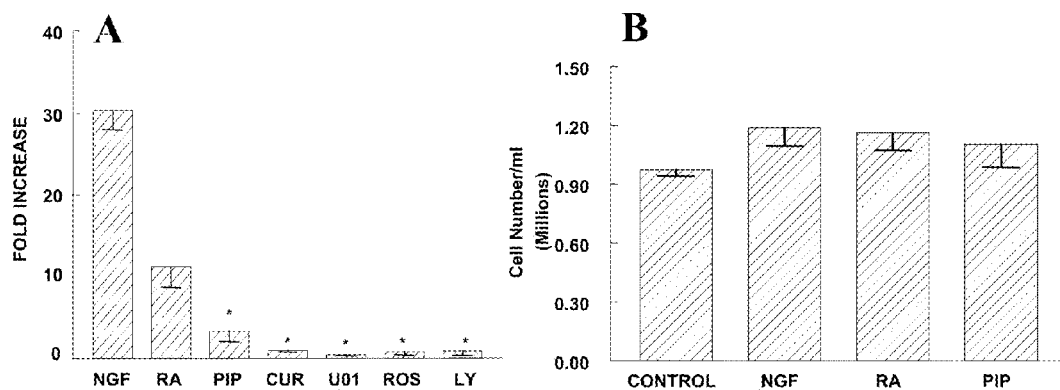
FIG. 9 depicts the effects of "hit" compounds on cell differentiation (panel A) and cell proliferation (panel B).

An ES cell line (ES-6; Preliminary Studies Section C.2.) containing a stably integrated necdin-puromycin-IRES-β-galactosidase cassette was allowed to form EB. Briefly, 1000 cells in 200 μl of media without LIF were plated into 96-well PCR plates. On the third day, the EB were transferred to 96-well tissue culture plates in which each well was coated with laminin. The medium was changed on the fourth day and appropriate small molecule compounds were added with each compound being assessed in triplicate. Six wells received no treatment and six wells received treatment with vehicle control (DMSO or ethanol diluted in similar manner as small molecule compounds). The cells were incubated with compounds for 48 hr, compounds removed by washing with PBS and cells allowed to grow and differentiate in media for 4 days. Cells were lysed on the fifth day and the lysates were analyzed for β-galactosidase expression. FIG. 9A shows the effects of the indicated compounds at 10 μM concentrations. Two positive controls, NGF and RA (Sigma Chemical, St. Louis) and five small molecule compounds (piperine, curcumin, rosmarinic acid, U0126, LY294002) were used for screening. Fold increase was calculated based on the respective vehicle control β-galactosidase activity. NGF showed more (30-fold) neurogenesis than did RA (11-fold). This is not surprising since NGF is a stronger neurogenic growth factor than is RA. Piperine had a 3.3-fold increase for neurogenesis that was significantly different statistically from the positive controls. However, since none of the test compounds displayed increases equal to or greater than the controls (NGF or RA), the interpretation of this high throughput screen is that none of these small molecules have neurogenesis potential. One interpretation of the piperine-induced slight (3.3-fold) increase in neurogenesis is that there is increased cell division; however, no significant increase in cell number was observed (FIG. 9B). Even though the 3.3-fold (slight) increase by piperine may be due to inhibition of other lineages or selective cell division events, the piperine result is not considered a hit because it is not equal to or greater than the positive controls (NGF, RA). As a reminder, in this developed screen assay, compounds will be defined as "hits" for subsequent validation only if they show results equal to or greater than those of the positive (NGF or RA) controls.

Example 4

EBs as Screening Tools

EB Formation for Screening Purposes

Applicant has developed a method of EB formation in a 96-well format for use in screening assays. The method involves growing ES cells (1,000/well) in 96-well sterile V-shaped wells of PCR microplates in 200 μl media for 3 days. Single uniform-sized EB in a multiwell format is preferred for experimental set-up of throughput studies. Since EB recapitulates embryogenesis, use of single uniform-sized EB in a multi-well format for the development of all cell types present in an adult organism is a powerful model system. For throughput studies, the potential exists that expensive animal studies can be eliminated since, in essence, EB represents an in vivo study of a developing organism in an in vitro scenario of EB in a multi-well format.

EB are transferred to tissue culture plates for differentiation and exposure to small molecule compounds, grown for indicated times (6, 8 and 12 days after small molecule exposure) and assayed for β-galactosidase expression. It has been shown that EB formed for 1 day and EB formed for 4 days, followed by RA treatment, differentiate into neuronal cells after plating onto tissue culture dishes [4, 32]. Thus, both early (e.g., 1 day for mouse) and later (e.g., 4 day for mouse) time points for drug treatment and differentiation end points in the instant screening assay are preferred. If any of the small molecule compounds cause an increase in expression of β-galactosidase, then further analysis may be done (e.g., immunocytochemistry) to verify differentiation into a specific cell lineage. To carefully evaluate any particular sub-type of neuronal cells generated by the treatment, neurons may be first enriched by selection. After exposure to the small molecule compound for an incubation time allowing for differentiation of predominantly neurons, the cells are treated with the selection drug puromycin (0.5 μg/ml). Applicants data indicate that by day 12 after selection, neurons are enriched (FIG. 6). The surviving cell population will be analyzed by immunocytochemistry for identification of neuronal sub-type that survived. An additional experiment to be performed is the screening of small molecule compounds (agents) can be screened by being added directly to ES cells. The compound is incubated with ES cells for 2-4 days in tissue culture plates after which time the compound is removed by washing in PBS buffer. ES cells are then cultured for different amounts of time in DMEM media and the differentiated status are analyzed at each time point.

β3-Galactosidase Activity as an Indicator of Post-Mitotically Differentiated Neurons After addition of puromycin to the media, neuronal cells are the anticipated survivors and other cell types are expected to be eliminated. Since activity of the necdin promoter confers β-galactosidase expression, a quantitative measurement of β-galactosidase activity is performed. Cells are lysed in lysis buffer (100 mM potassium phosphate, pH 7.8, 0.2% Triton X-100, 1 mM dithiothreitol) and lysates are obtained at different time points (days of culture for ES cell differentiation). β3-galactosidase activity is measured using β-galacton, a chemiluminogenic substrate [29] that is very sensitive for detection of β-galactosidase activity. Activity is normalized to the total protein content of the cell lysates using the BCA method (Pierce Chemical, Rockford, Ill.). The negative control is differentiated ES cells without a targeted promoter-selection-reporter cassette. Negative control lysate is used as background and varying amounts of purified *E. coli* β-galactosidase enzyme (Sigma Chemical, St. Louis, Mo.) is added to the negative control lysate to produce a positive control for β-galactosidase activity.

Immunocytochemisty

For in situ immunofluorescence, cells are grown on laminin-coated coverslips, rinsed with Tris-buffered saline (TBS: 50 mM Tris-HCl, pH 7.5, 150 mM, NaCl) and fixed with 4% paraformaldehyde in TBS for 10 min. Cells are washed with TBS and incubated with primary antibody in 1% BSA, 05% Triton X100 (overnight, 4° C.). Cells are washed with TBS and incubated with fluorescein isothiocyanate (FITC)-conjugated secondary antibody or rhodamine-conjugated secondary antibody or Alexa 488 or Alexa 568 conjugated secondary antibody in TBS containing 0.05% Triton X100 and 1% BSA for 30 min. Cell types are visualized using fluorescence microscopy. To verify that indeed the cells are neuronal, indirect immunofluorescence is performed to detect the low affinity NGF receptor (p75) and the MAP2 neurofilament (commonly used neuronal cell markers). Briefly, cells are fixed and incubated with anti-MAP2 (a+b) monoclonal antibody (Sigma Chemical) followed by Oregon Green conjugated secondary antibody or with antibody to the low affinity NGF receptor (Chemicon) followed by rhodamine conjugated secondary antibody (Molecular Probes). FIGS. 3, 5 and 7 in Preliminary Studies provide examples of ES cells differentiated with RA into neurons which stain positive for MAP2 and low affinity NGF receptor and have a typical neuronal morphology. Neuronal cells present on day 12 of differentiation also express β-galactosidase as determined by indirect immunofluorescence with anti-β-galactosidase antibody (Roche) followed by Oregon Green conjugated secondary antibody (Molecular Probes) (FIG. 4 of Preliminary Studies). This result indicates that the necdin promoter drives expression of the lacZ gene and that the necdin promoter is active in differentiated neuronal cell types. If a particular small molecule compound shows preferential neuronal differentiation, further immunocytochemistry is performed to determine neuronal subtype formed. FIG. 7 shows double immunostaining for β-galactosidase and the neuronal marker, low affinity NGF receptor (p75). The neuron stains for both markers indicating that β-galactosidase reporter expression occurs only in neurons (Preliminary Studies Section C.2.).

From the screening of agents (e.g., small molecules), it is reasonable to expect that one or several compounds show effects on neuronal cell lineage formation. Interpretation of a compound's effect on a specific differentiated cell lineage without an understanding of effects on other cell lineages does not provide a solid overall picture of occurrences at the organismal level. For example, a compound may exert its effect on ES cell differentiation along a neuronal lineage by a novel mechanism of action which itself may be of importance to study mechanisms of neurogenesis. The mechanism may be either that the compound selectively acts on the differentiation pathway of a particular type or lineage of cells or that the compound inhibits other cell lineages thereby preferentially allowing a particular lineage or cell type to differentiate and survive. This strategy reduces the use of animals and embryos and also is more cost-effective. Additionally, studying the effect of small molecules on EB sheds more light on their mechanism of action than does a similar study in a single type of cells. For example, the drug thalidomide showed no anti-angiogenic effect when screened in an endothelial cell culture system or chorioallantoic membrane assay; however, since use of EB recapitulates intact embryo development, it was demonstrated that thalidomide had anti-angiogenic effects [17].

Example 5

Single Embryoid Body Formation in a Multiwell Plate

The following references are cited as superscripts throughout this example (infra). They are incorporated herein by reference. They serve to illustrate and enable the invention. Applicant reserves the right to challenge the veracity of any statement(s) therein made.
1. Bain, G., D. Kitchens, M. Yao, J. E. Huettner and D. I. Gottlieb. 1995. Embryonic stem cells express neuronal properties in vitro. Dev Biol 168:342-357.
2. Chen, D., R. L. Lewis and D. S. Kaufman. 2003. Mouse and human embryonic stem cell models of hematopoiesis: past, present, and future. Biotechniques 35:1253-1261.
3. Dang, S. M., M. Kyba, R. Perlingeiro, G. Q. Daley and P. W. Zandstra. 2002. Efficiency of embryoid body formation and hematopoietic development from embryonic stem cells in different culture systems. Biotechnol Bioeng 78:442-453.
4. Ding, S. and P. G. Schultz. 2004. A role for chemistry in stem cell biology. Nat Biotechnol 22:833-840.
5. Doetschman, T., M. Shull, A. Kier and J. D. Coffin. 1993. Embryonic stem cell model systems for vascular morphogenesis and cardiac disorders. Hypertension 22:618-629.
6. Evans, M. J. and M. H. Kaufman. 1981. Establishment in culture of pluripotential cells from mouse embryos. Nature 292:154-156.
7. Fernandez, L. A., E. W. Hatch, B. Armann, J. S. Odorico, D. A. Hullett, H. W. Sollinger and M. S. Hanson. 2005. Validation of large particle flow cytometry for the analysis and sorting of intact pancreatic islets. Transplantation 80:729-737.
8. Gerecht-Nir, S., S. Cohen, A. Ziskind and J. Itskovitz-Eldor. 2004. Three-dimensional porous alginate scaffolds provide a conducive environment for generation of well-vascularized embryoid bodies from human embryonic stem cells. Biotechnol Bioeng 88:313-320.
9. Kumar, D., T. J. Kamp and M. M. LeWinter. 2005. Embryonic stem cells: differentiation into cardiomyocytes and potential for heart repair and regeneration. Coron Artery Dis 16:111-116.
10. Kurosawa, H., T. Imamura, M. Koike, K. Sasaki and Y. Amano. 2003. A simple method for forming embryoid body from mouse embryonic stem cells. J Biosci Bioeng 96:409-411.
11. Liersch, R., F. Nay, L. Lu and M. Detmar. 2006. Induction of lymphatic endothelial cell differentiation in embryoid bodies. Blood 107:1214-1216.
12. Muthuchamy, M., L. Pajak, P. Howles, T. Doetschman and D. F. Wieczorek. 1993. Developmental analysis of tropomyosin gene expression in embryonic stem cells and mouse embryos. Mol Cell Biol 13:3311-3323.
13. Risau, W., H. Sariola, H. G. Zerwes, J. Sasse, P. Ekblom, R. Kemler and T. Doetschman. 1988. Vasculogenesis and angiogenesis in embryonic-stem-cell-derived embryoid bodies. Development 102:471-478.
14. Smith, A. G. 2001. Embryo-derived stem cells: of mice and men. Annu Rev Cell Dev Biol 17:435-462.

Murine ES cells are pluripotent and derived from the inner cell mass of an early embryo. When cultured in the presence of anti-differentiation agents such as leukemia inhibitory factor (LIF) and embryonic fibroblasts, these cells maintain their pluripotency and have the ability to differentiate into any cell type of the body[1;2;6;14]. Removal of the anti-differentiation agent causes the ES cell to spontaneously differentiate which follows a reproducible temporal pattern and in many ways recapitulates early embryogenesis. When ES cells are cultured in suspension without anti-differentiation agents, they form three dimensional aggregates called embryoid bodies (EB). In culture, EB give rise to all three germ layers, and over time, differentiate into a wide variety of cell types, such as cardiomyocytes, hematopoietic cells, neurons, pancreatic islet cells, etc[1;3;11;13;14].

Therefore, EB, which give rise to all types of cells and recapitulate events similar to those during embryonic development, are an ideal system to study effects of small molecules and/or biological agents instead of using embryos or whole animals. To develop such a screening system, it is essential to assess EB with a throughput screening format. Of importance, having single uniform-sized EB in a well is preferred because this format provides uniformity in EB differentiation that is critical in comparison studies of diverse compounds and biological agents. Most preferably the uniform size is about 415 nm±50 nm. Current techniques for EB assessment include hanging drop and suspension methodologie[3;8]. The hanging drop method provides uniform sizes of EB but this technique is challenging to perform and is not amenable to throughput screening strategies. The suspension culture method gives rise to nonuniformly sized cells. Current methods that ensure uniform sizes of EB in a screening format are not simple procedures and require the use of sophisticated flow sorting equipment[7]. Additionally, to dispense single EB into wells by currently available automated methods is not cost-effective. For this reason, a simple, cost effective method in which EB can be generated of uniform size and single EB can be dispensed per microwell is herein described in a manner amenable to throughput methodologies for screening purposes. Theoretically, one can consider a single EB in a well as an equivalent to a developing embryo, or in other words, a single EB is a developing organism in a microwell. The method described here allows screening and testing of biochemical compounds, biological agents, infectious organisms and also allows for toxicity evaluation.

ES cells derived from 129/SvJ mice were maintained in culture on a layer of feeder cells consisting of mitomycin C treated primary mouse embryonic fibroblasts (MEF). The ES cells were cultured in ES medium (DMEM media supplemented with 15% serum [Hyclone, Logan, Utah], 1000 units/ml LIF [ESGRO from Chemicon, Temecula, Calif.], 1 mM sodium pyruvate, 1 mM nonessential amino acids, 0.1 mM 2-mercaptoethanol, 25 units/ml penicillin and 25 µg/ml streptomycin). The ES cells were plated onto a prepared feeder layer with freshly made ES medium and incubated in a humidified incubator (37° C., 5% $CO_2$). The media was changed every other day. ES cells were cultured in the absence of feeder cells in a pre-differentiation step to remove feeder cells from the culture. To accomplish this, ES cells were passaged onto 0.1% gelatin-coated tissue culture plates. For differentiation, the ES cells were washed with phosphate buffered saline (PBS), trypsinized, dissociated into single cells and suspended in differentiation media that is the same formulation as ES medium except it is devoid of LIF. The cell number was adjusted to $5\times10^3$ cells/ml.

To achieve single EB with uniformity of size, approximately 1,000 ES cells in a 200 µl volume were dispensed into sterile 96 well polyvinyl carbonate polymerase chain reaction (PCR) plates (Greiner Bio-One Inc, Longwood, Fla.), tapped gently and incubated (4 d, 37° C., 5% CO2). Number of EB/well was counted on the fourth day. Table 2 shows results of four independent experiments to determine number of EB per well using the described method. The predominant number of EB/well was one (92%, 97%, 95%, 93% of the wells in a 96 well multiwell plate had single EB) with an average of 94% of the wells having a single EB. Two EB/well were observed 6% (mean value of n=4) of the time. More than two EB/well were never observed. To obtain a mean value for EB size, single EB (n=17 to 20) were randomly picked from three experiments and diameter of the EB was measured. Mean average diameter of the EB was 415 microns. A photomicrograph of a single EB in a well format is displayed (FIG. 1B) and a well containing more than one EB is presented (FIG. 1A). As stated above, the most frequent observation was a single EB/well in this format or rarely, two EB/well were evident in which case the EB were either uniform or dissimilar in size by this method.

The differentiation of the single EB/well format was demonstrated by the ability of EB to give rise to differentiated cardiac muscle cells[5;10;12]. EB grown for 4 days were transferred from a 96 well PCR plate using a multichannel pipette into a 96 well tissue culture plate coated with gelatin (as stated above). The EB in each well were periodically observed microscopically for generation of a specific characteristic, a beating cardiac muscle phenotype, in the population of cells derived from the EB in each well. From days 3 to 7, beating cardiac muscle cells were observed in all wells.

EB formed from murine ES cells recapitulate many aspects of a developing embryo. Synchronous differentiation of EB is achieved by formation of uniformly sized EB. The method demonstrated in this report is easy to perform and is cost-effective. Additionally, a large number of EB can be generated using the 96 well PCR plate method followed by transferring the EB to 96 well tissue culture plates for differentiation and screening purposes. The differentiation of ES cells into various lineages is a highly studied area largely because of the direct applicability of ES cells to the field of regenerative medicine[4;9;14].

TABLE 2

MOST WELLS (94%) IN 96-WELL MICROPLATE FORMAT SUPPORT GROWTH OF A SINGLE EMBRYOID BODY.

| | One Embryoid Body | | Two Embryoid Bodies | |
|---|---|---|---|---|
| | Raw Data | % Total | Raw Data | % Total |
| 1 | 88 | 92 | 9 | 8 |
| 2 | 93 | 97 | 3 | 3 |
| 3 | 91 | 95 | 5 | 5 |
| 4 | 89 | 93 | 7 | 7 |
| | 361/384 wells | 94%* | 24/384 wells | 6% |

*= $p < 0.001$ versus wells with 2 EB

What is claimed is:

1. A method for making mouse embryoid bodies having a uniform size, comprising (a) genetically modifying a mouse embryonic stem (ES) cell to contain a transgene comprising a reporter gene and selectable marker, both operably linked to a developmentally regulated promoter and operably separated by an internal ribosome entry site (IRES), (b) growing the ES cells in the presence of feeder cells and leukemia inhibitory factor (LIF), (c) removing the feeder cells, (d) dissociating the ES cells in differentiation media, (e) placing approximately 1,000 dissociated ES cells of step (d) in a 200 µl volume into each well of a plurality of wells of a polyvinyl carbonate multiwell plate in media, wherein the multiwell plate is not subjected to centrifugation and a single mouse embryoid body (EB), that has a uniform diameter relative to other EBs formed in, is produced per well in at least 92% of the wells.

2. The method of claim 1 wherein the uniform diameter is approximately 415 nm±10%.

3. The method of claim 1 wherein the developmentally regulated promoter is a necdin promoter.

4. The method of claim 1 wherein the reporter gene is lac Z and the selectable marker gene is a puromycin-resistance gene.

5. A system comprising a plurality of embryoid bodies in a polyvinyl carbonate plate having multiple wells, the embryoid bodies formed according to steps of (a) introducing a genetic construct into a mouse embryonic stem (ES) cells, (b) growing said ES cells in the presence of feeder cells and LIF, (c) removing the feeder cells, (d) dissociating the ES cells in differentiation media, (e) placing approximately 1,000 ES cells in a 200 µl volume into each individual well of the plate having multiple wells, wherein the plate is not subjected to centrifugation such that embryoid bodies (EB) are produced that have a uniform diameter relative to other EBs formed in other wells; and wherein (f) one or more embryoid body contains a genetic construct, and (g) at least 92% of the wells contain a single embryoid body, wherein the genetic construct comprises a developmentally-regulated promoter operably linked to a selection marker and a reporter marker that are operably separated by an IRES.

6. The system of claim 5 wherein the developmentally-regulated promoter is a necdin promoter, the selection marker is a puromycin-resistance gene, and the reporter marker is a lac Z gene.

7. The system of claim 5 wherein the uniform diameter is approximately 415 nm±10%.

* * * * *